(12) United States Patent
Hill

(10) Patent No.: US 12,337,131 B2
(45) Date of Patent: *Jun. 24, 2025

(54) VARIABLE FREQUENCY WAVEFORM TATTOO NEEDLE MECHANISM

(71) Applicant: Carson F Hill, Thousand Oaks, CA (US)

(72) Inventor: Carson F Hill, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/761,645

(22) Filed: Jul. 2, 2024

(65) Prior Publication Data

US 2025/0032765 A1 Jan. 30, 2025

Related U.S. Application Data

(63) Continuation of application No. 17/283,198, filed as application No. PCT/US2020/063828 on Dec. 8, 2020, now Pat. No. 12,023,461.

(60) Provisional application No. 63/122,361, filed on Dec. 7, 2020, provisional application No. 62/945,625, filed on Dec. 9, 2019.

(51) Int. Cl.
*A61M 37/00* (2006.01)

(52) U.S. Cl.
CPC ... *A61M 37/0076* (2013.01); *A61M 2205/103* (2013.01); *A61M 2205/586* (2013.01)

(58) Field of Classification Search
CPC ......... A61M 37/0076–0084; A61M 2205/103; A61M 2210/04; A61M 2250/00; A61M 5/46; A01K 11/005; A61B 17/32093; A61B 2017/00398; A61B 2017/00477
See application file for complete search history.

(56) References Cited

U.S. PATENT DOCUMENTS

2005/0010236 A1* 1/2005 Frister ............... A61M 37/0076
606/116
2022/0118239 A1* 4/2022 Wang ................ A61M 37/0076

FOREIGN PATENT DOCUMENTS

KR 20190009995 A * 1/2019

* cited by examiner

*Primary Examiner* — Brigid K Byrd
(74) *Attorney, Agent, or Firm* — Mark R. Kendrick

(57) ABSTRACT

A rotary tattoo machine includes an inner housing; a tattoo needle; an electric motor including a shaft assembly; and a bearing arm including a bearing. The machine also includes a cam, the cam moving up and down the shaft assembly due to the rotation of the shaft assembly and the bearing, the moving of the cam to drive the tattoo needle from a retracted position to an extended position. The device my also include an outer housing or grip. The dimensions of or a shape of the cam reduces an amount of dwell time of the tattoo needle. The cam may be replaced by an alternate cam, the alternate cam having different dimensions or a different shape from the dimensions of or the shape of the original cam and the alternate cam to have a different amount of dwell time associated with the tattoo needle.

17 Claims, 11 Drawing Sheets

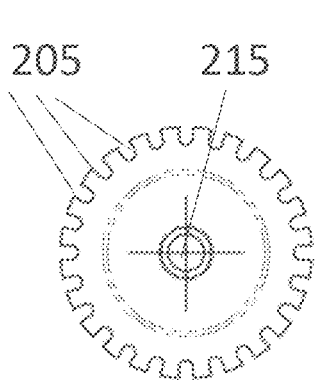
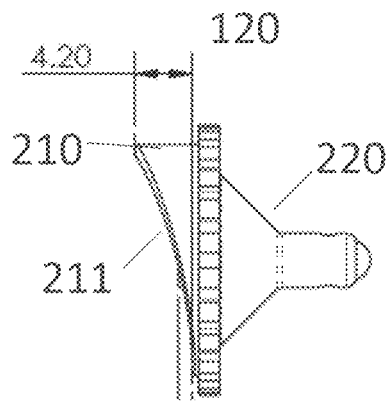
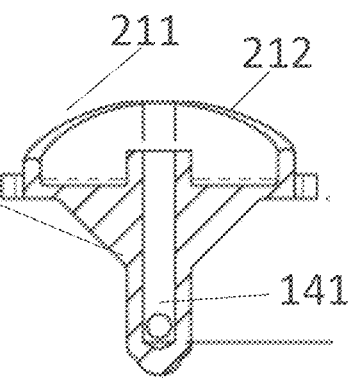
Figure 2A Figure 2B Figure 2C
4.2 28%
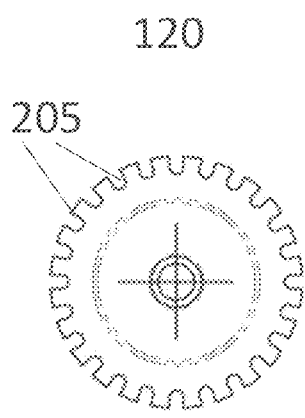
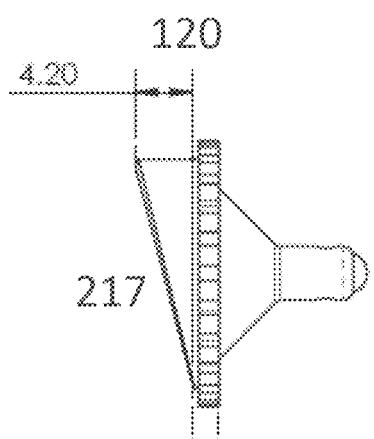
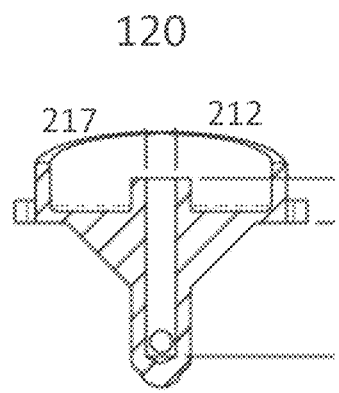
Figure 2D Figure 2E Figure 2F
4.2 40%

4.2 33%

4.2 20%

VARIABLE FREQUENCY WAVEFORM TATTOO NEEDLE MECHANISM

RELATED APPLICATIONS

This application claims priority to and is a continuation of U.S. non-provisional patent application Ser. No. 17/283,198, filed Apr. 6, 2021, which is a National Phase filing of Patent Cooperation Treaty (PCT) patent application serial No. PCT/US20/63828, filed Dec. 8, 2021, which claims priority to U.S. provisional patent application Ser. No. 63/122,361, filed Dec. 7, 2020, entitled "Variable Frequency Waveform Tattoo Needle Mechanism," and Ser. No. 62/945,625, filed Dec. 9, 2019, entitled "Variable Frequency Waveform Tattoo Needle Mechanism.".

BACKGROUND OF THE INVENTION

Rotary tattoo machines or devices cause a needle to hesitate inside the skin before being retracted due to a geometry of cams or cam assemblies that are used to drive a needle. This dwell or hesitation can cause added and unnecessary tissue damage being that an artist's hand may be moving forward and a needle is not given sufficient time to be retracted from the skin before such hand movement is made.

Rotary or cam driven tattoo machines can be very aggressive and/or damaging to skin tissue, which can cause, scar tissue, poor healing and/or extended healing times for skin tissue. This can leave a healing tattoo more susceptible to potential infections.

A stroke cycle means an amount of time it takes for a tattoo needle to move from a retracted position to a displaced position and then back to the retracted position. In other words, a stroke cycle is a timeframe where the action of the tattoo needle moves from the retracted position to the extended position and then returns to the retracted position.

BRIEF DESCRIPTION OF THE DRAWINGS

FIG. 2A illustrates a top view of a cam assembly having a stroke length of approximately 4.2 millimeters and a 28% dwell time according to some embodiments;

FIG. 2B illustrates a side view of a cam assembly having a stroke length of approximately 4.2 millimeters and a 28 percent dwell time according to some embodiments;

FIG. 2C illustrates a front cross-section view of a cam assembly having a stroke length of approximately 4.2 millimeters and a 28 percent dwell time according to some embodiments;

FIG. 2D illustrates a top view of a cam assembly having a stroke length of approximately 4.2 millimeters and a 40% dwell time according to some embodiments;

FIG. 2E illustrates a side view of a cam assembly having a stroke length of approximately 4.2 millimeters and a 40% dwell time according to some embodiments;

FIG. 2F illustrates a front cross-section view of a cam assembly having a stroke length of approximately 4.2 millimeters and a 40 percent dwell time according to some embodiments;

DETAILED DESCRIPTION OF THE INVENTION

Figure 1A:
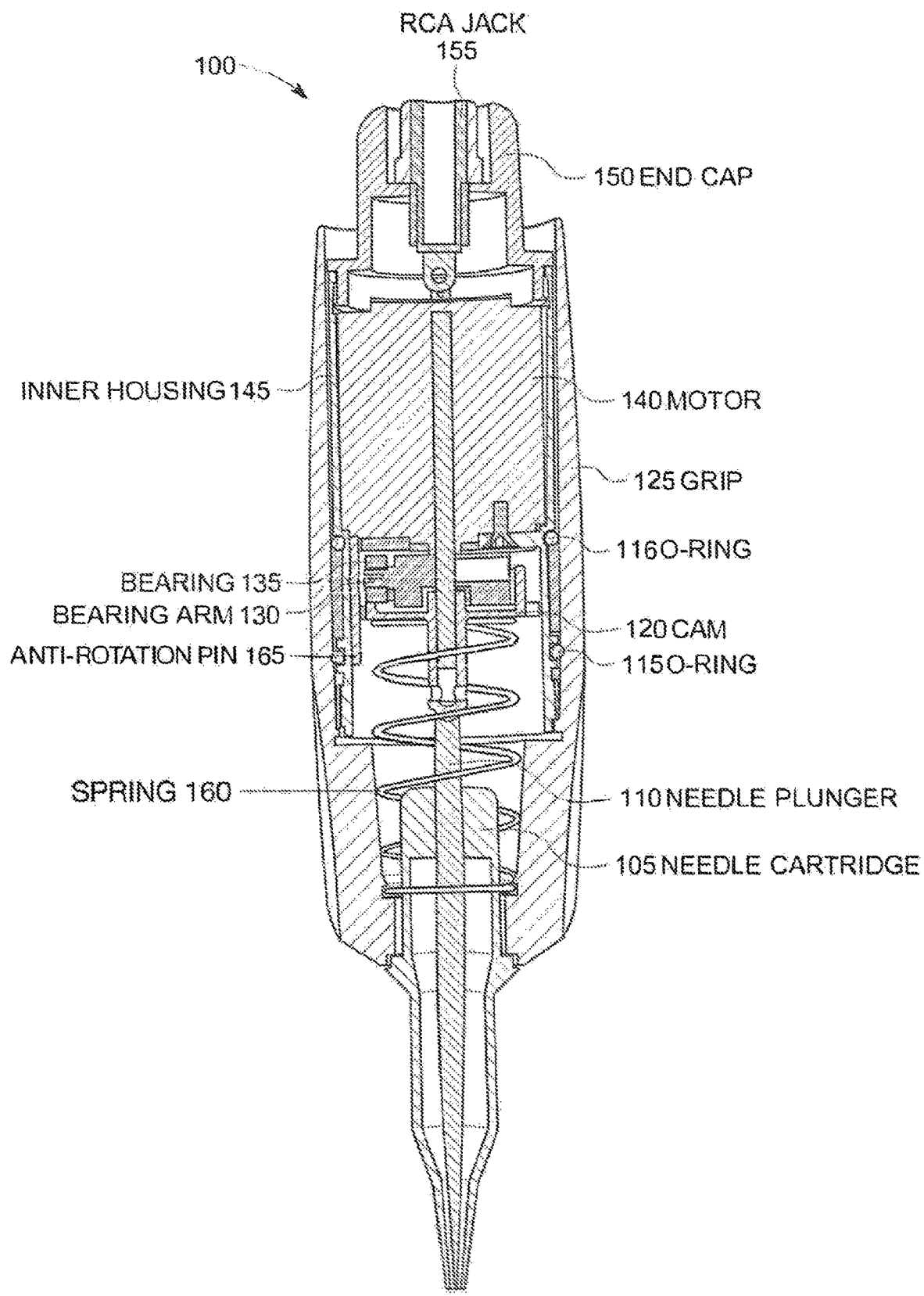
FIG. 1A illustrates a cross-sectional view of a rotary tattoo device or machine according to some embodiments.

The following description is not to be taken in a limiting sense, but is made merely for the purpose of describing the general principles of exemplary embodiments. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The following detailed description provides a better understanding of the features and advantages of the claimed subject matter described in the present disclosure in accordance with the embodiments disclosed herein. Although the detailed description includes many specific embodiments, these are provided by way of example only and should not be construed as limiting the scope of the claimed subject matter disclosed herein.

In the following detailed description, exemplary embodiments in which various aspects of the disclosure may be practiced are described in sufficient detail to enable those skilled in the art to practice the claimed subject matter. It is to be understood that other embodiments may be utilized and that logical, programmatic, mechanical, electrical and other changes may be made without departing from the spirit or scope of the present disclosure. The following detailed description is, therefore, not to be taken in a limiting sense, and the scope of the present disclosure is defined by the claims and equivalents thereof.

The description of the illustrative embodiments can be read in conjunction with the accompanying figures. Embodiments incorporating teachings of the present disclosure are shown and described with respect to the figures presented herein. The specific numerals assigned to the elements are provided solely to aid in the description and are not meant to imply any limitations (structural or functional or otherwise) on the described embodiment. It will be appreciated that for simplicity and clarity of illustration, elements illustrated in the figures have not necessarily been drawn to scale. For example, the dimensions of some of the elements are exaggerated relative to other elements.

It is understood that the use of specific component, device and/or parameter names, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

Those of ordinary skill in the art will appreciate that the hardware components and basic configurations depicted in the figures may vary. The illustrative components are not intended to be exhaustive, but rather are representative to highlight essential components that are utilized to implement aspects of the described embodiments. For example, other devices/components may be used in addition to or in place of the hardware and/or firmware depicted. The depicted example is not meant to imply architectural or other limitations with respect to the presently described embodiments and/or the general claimed subject matter.

This claimed subject matter is directed to a device that is designed so that a speed and acceleration within a given stroke cycle of one or more needle(s) used to form a tattoo can be controlled. The claimed subject matter herein allows a tattoo artist or operator to control a degree or percentage of the dwell or hesitation time of a needle(s) inside a consumer's skin. In some embodiments, a dwell time may be reduced to 40 percent of a stroke cycle and in other embodiments, a dwell time can be reduced to 20 percent of a stroke cycle. Additionally, in some embodiments, a dwell or hesitation time can be varied for different tattooing types or styles (e.g., lining, shading, coloring, black work, color or other types or styles of tattooing). In the claimed subject matter, the cam or cam assembly is replaceable and/or interchangeable and may control a timeframe or dwell time that a tattoo needle is inside a consumer's skin or in an extended position by having different dimensional measurements and/or shapes and/or characteristics.

In embodiments, the variable waveform cam device or apparatus may cause the needle(s) to be retracted from the consumer's skin much quicker, which reduces trauma inflicted on the consumer's skin tissue. In some embodiments, the cam or cam assembly may be replaceable or be able to be changed. In this embodiment, the cam or cam assembly may also be changed to a different geometric configuration and/or shape to allow an artist to determine a most effective amount of dwell or hesitation time. In some embodiments, the cam or cam assembly may be changed to allow a tattoo artist to control a dwell time or hesitation to occur in whatever position or portion of the stroke cycle the tattoo artist wants (e.g., expansion and/or extraction), and to be utilized for whatever tattooing effect the tattoo artist is aiming to achieve.

The claimed subject matter differs from currently available tattoo devices or machines in many ways. There are no similar devices or mechanisms within the tattoo industry to date. No tattoo machines include a cam or cam assembly similar to the cam described herein. Previous tattoo devices or mechanisms have no way of controlling an amount of dwell or hesitation time of the needle(s) in any position of a stroke cycle. Further, previous tattoo devices or mechanisms also have no way to control the speed or acceleration of the needle(s) in any position of a stroke cycle. In some embodiments, the claimed subject matter is directed to the ability to adjust and/or control a) the dwell or hesitation time of a needle in a consumer's skin and b) the speed or acceleration of the needle in the tattoo machine within a given stroke cycle. Further, the claimed subject matter enables an artist to vary the amount of time a needle(s) spends in the skin or in an extended position in order to reduce trauma to skin and in order to best saturate a tattoo. In addition, the cam or cam assembly has a unique design that includes one or more receptacle areas or slots or openings that allow an anti-rotation pin to be utilized to keep the cam or cam assembly from rotating.

Many consumers are unaware that their tattoo machines or devices are causing the needle(s) they are using to dwell or hesitate inside the skin as they are tattooing, and so no measures are in place or being used to reduce the trauma associated with this needle dwell.

Figure 1B:
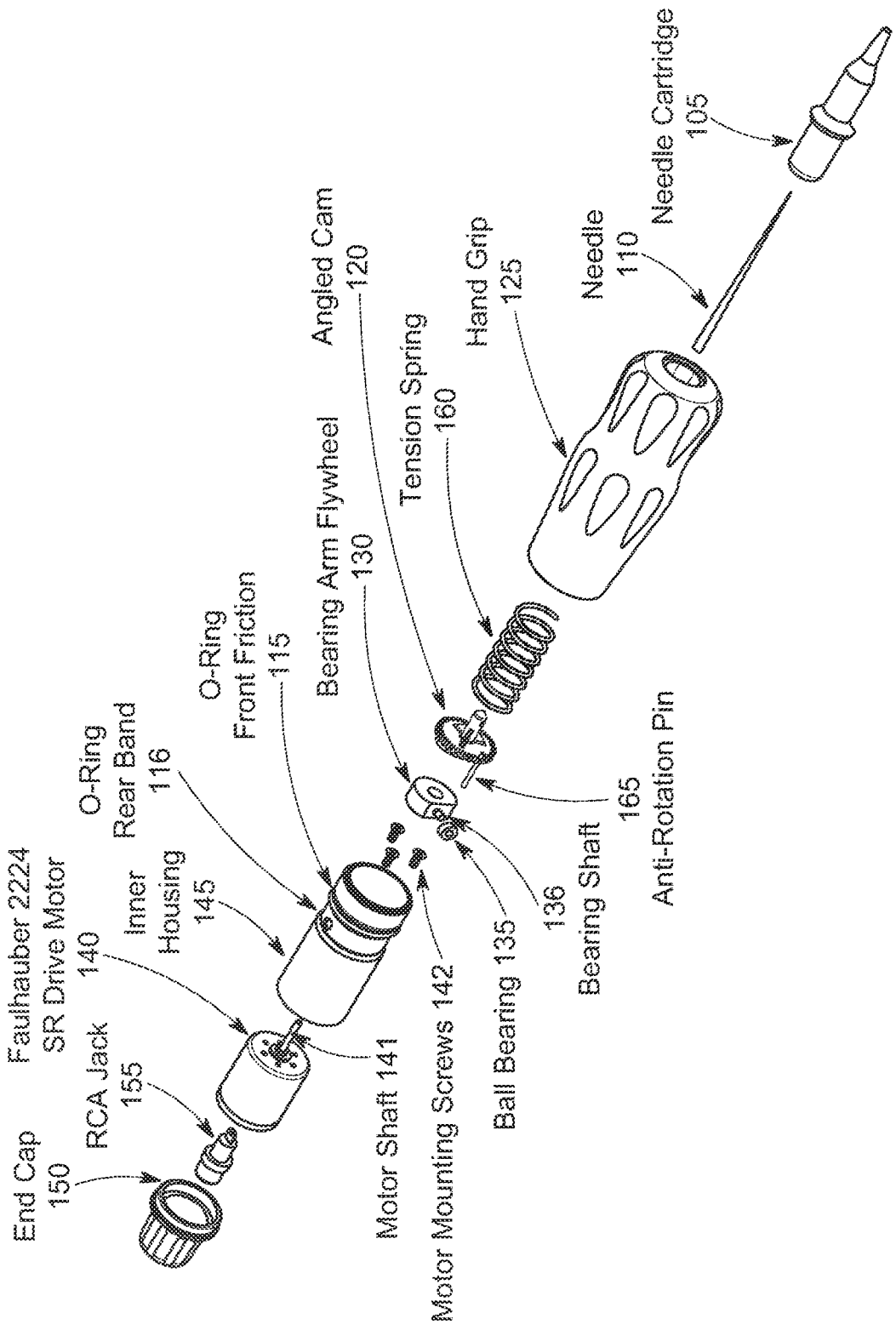
FIG. 1B illustrates an exploded view of a rotary tattoo device or machine according to some embodiments.

FIG. 1A illustrates a cross-sectional view of a rotary tattoo device or machine according to some embodiments. FIG. 1B illustrates an exploded view of a rotary tattoo device or machine according to some embodiments. In some embodiments, a rotary tattoo device or machine 100 may include a RCA jack or power input port 155; an end cap 150, an inner housing 145, an electric motor or motor assembly 140, a motor shaft assembly 141, a bearing 135, a bearing arm or flywheel 130, a bearing shaft or post 136, a grip or grip assembly 125, at least two O-rings (a rear O-ring 116 and a front friction O-ring 115), a replaceable cam or cam assembly 120, a needle plunger or a needle 110 and/or a needle cartridge 105.

In some embodiments, the electrical motor or motor assembly 140 may be positioned or attached to the inner housing 145. In some embodiments, the electrical motor or motor assembly 140 may be attached via one or more machine screws 142 although other fasteners may be utilized. In some embodiments, the motor or motor assembly 140 may have a cylindrical or circular shape. In some embodiments, the inner housing 145 may have a cylindrical or circular shape. In some embodiments, the diameter of the inner housing 145 may be reduced from one end to another. In some embodiments, a motor shaft 141 may be attached, connected and/or coupled to the electrical motor assembly 140 (or may be integrated within the electrical motor assembly 140).

In some embodiments, a bearing arm or flywheel 130 may be connected, coupled or attached to the motor shaft 141. In some embodiments, the bearing arm or flywheel 130 may have a hole or opening in its center into which the motor shaft 141 may be inserted. In some embodiments, the bearing arm or flywheel 130 may be connected and/or attached to the motor shaft 141 via a set screw or other fasteners.

In some embodiments, the bearing arm or flywheel 130 may have a bearing 135 press fit onto a bearing shaft 136 that may be built in or attached to the bearing arm or flywheel 130. In some embodiments, the bearing arm or flywheel 130 may have a circular shape with one flat side, or alternatively may have a number of other shapes. In some embodiments, the bearing shaft 136 may protrude from or be attached to an outer surface of the bearing arm or flywheel 130.

In some embodiments, the replaceable cam or cam assembly 120 may be coupled, connected, attached or fit onto an end (e.g., a distal end) of a motor shaft 141. In some embodiments, the cam or cam assembly may have a circular shape. In some embodiments, the cam or cam assembly 120 may have one or more teeth, slots or openings on a circumferential edge of the cam or cam assembly 120. In some embodiments, the cam or cam assembly 120 may have a protrusion on a first end to receive the motor shaft 141. In this embodiment, the motor shaft 141 may be positioned inside the protrusion of the cam or cam assembly 120. In some embodiments, a second end of the cam or cam assembly [141] 120 may include an angled ramp, a ramp feature, a ramp shape or a ramp portion. The angle, shape and/or dimensions of the ramp feature or ramp portion of the cam or cam assembly are novel and allow an operator to control a dwell time or hesitation time of the needle in a user's skin and/or in an extended position. In some embodiments, the ramp feature or ramp portion may have a shape that resembles a waveform (e.g., like a ramp waveform, a sinusoidal waveform, or a curved pulse waveform). In some embodiments, different waveforms may correspond to different cam or cam assemblies and thus they may be variable.

Figure 1C:
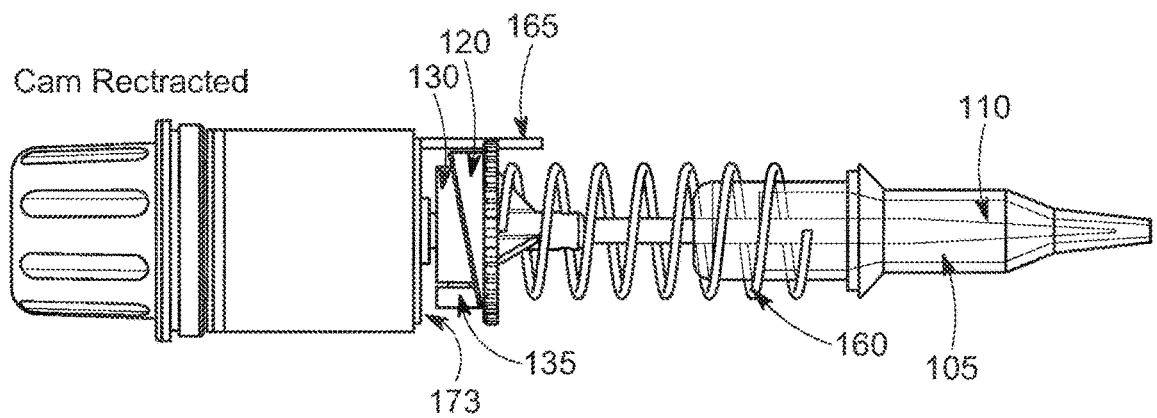
FIG. 1C illustrates a side view of a rotary tattoo machine in a retracted position with an outer cover or grip removed according to some embodiments.
Figure 1D:
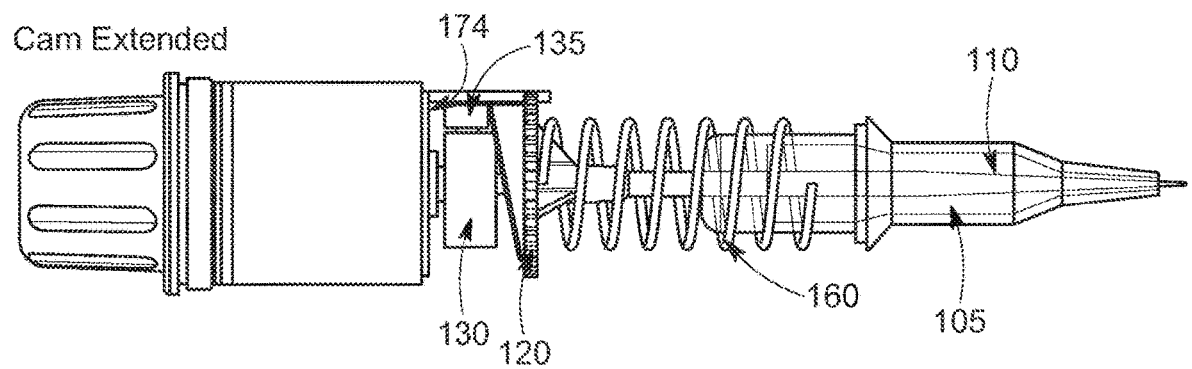
FIG. 1D illustrates a side view of a rotary tattoo machine in an extended position with an outer cover or grip removed according to some embodiments.
Figure 1E:
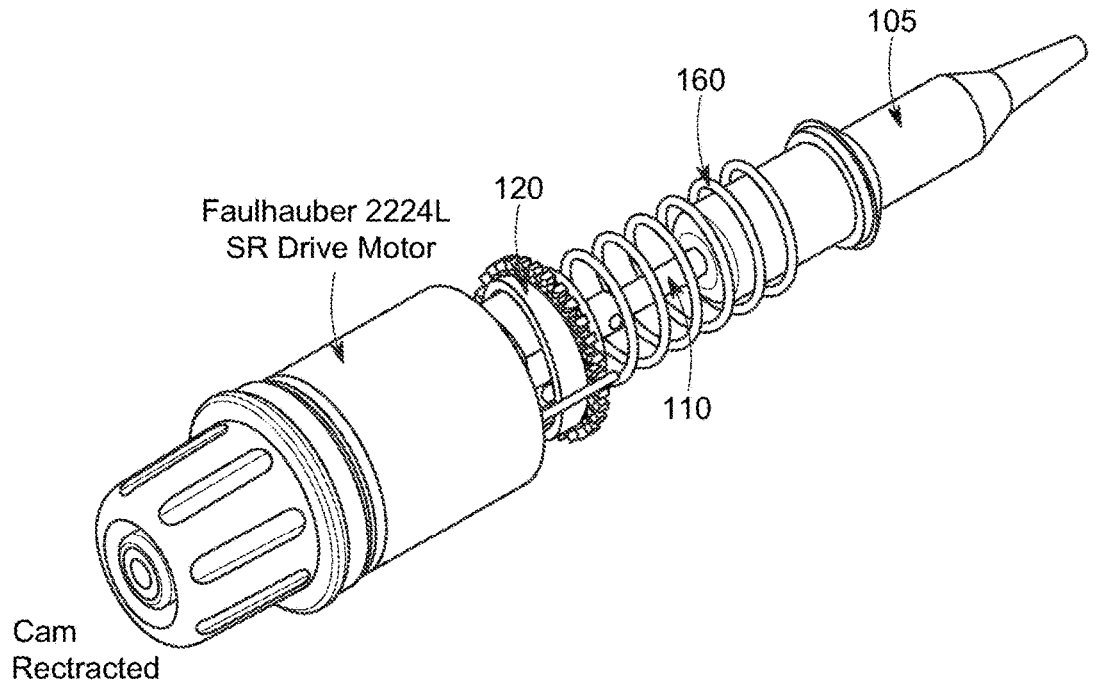
FIG. 1E illustrates a top perspective view of a rotary tattoo machine in a retracted position with a grip removed according to some embodiments.
Figure 1F:
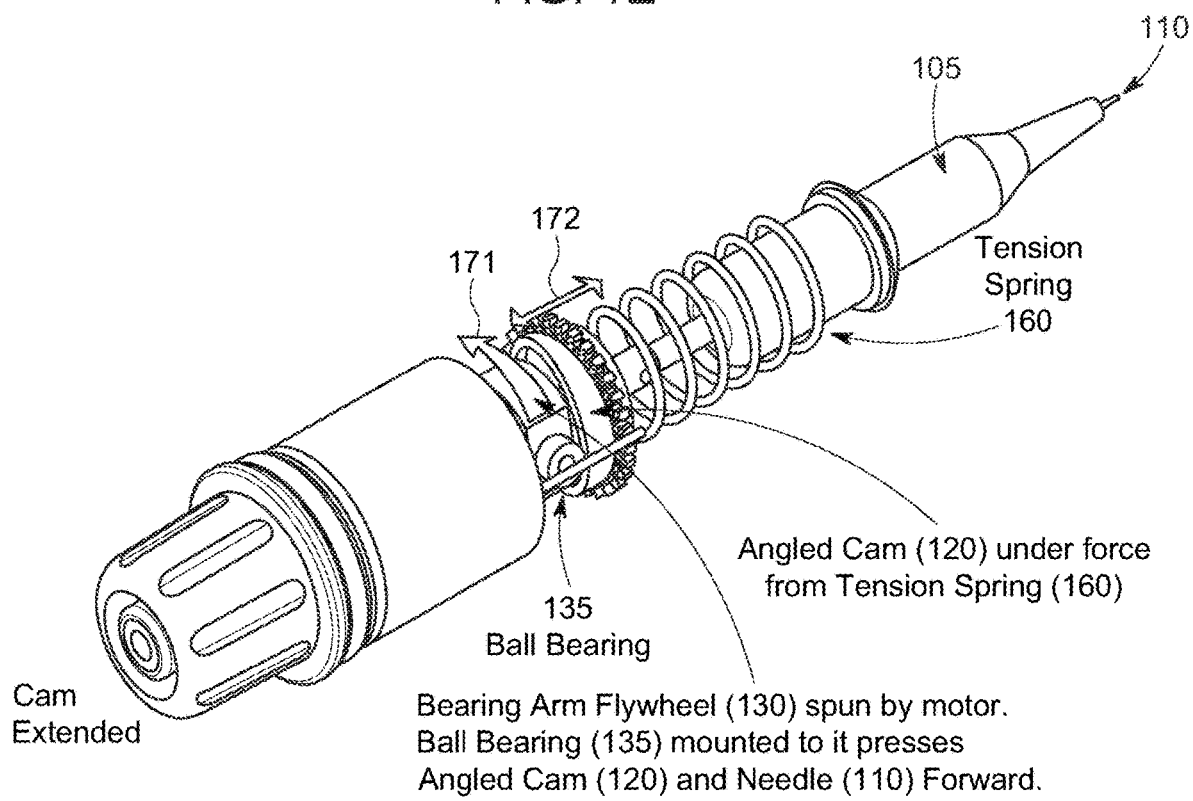
FIG. 1F illustrates a top perspective view of a rotary tattoo machine in an extended position according to some embodiments.

FIG. 1C illustrates a side view of a rotary tattoo machine in a retracted position with an outer cover or grip removed according to some embodiments. FIG. 1D illustrates a side view of a rotary tattoo machine in an extended position with an outer cover or grip removed according to some embodiments. FIG. 1E illustrates a top perspective view of a rotary tattoo machine in a retracted position with a grip removed according to some embodiments. FIG. 1F illustrates a top perspective view of a rotary tattoo machine in an extended position according to some embodiments. In some embodiments, the replaceable cam or cam assembly 120 may slide up or down the motor shaft 141 during operation of the rotary tattoo device or machine 100. In some embodiments, as the motor assembly 140 is turned on, the motor shaft 141 rotates in a clockwise or counterclockwise direction. In some embodiments, the motor shaft 141 rotation causes the bearing arm or flywheel 130 to rotate as illustrated by reference number 171 in FIG. 1F. In some embodiments, the bearing arm flywheel 130 rotation may cause the bearing 135 to move from a first position 173 (needle in a retracted position) to a second position 174 (needle in an extended position) as is illustrated in FIGS. 1C and 1D. As is illustrated in FIGS. 1C and 1D, the bearing 135 moves up the ramp feature or ramp shape of the cam 120 and this movement causes the cam 120 to move to the extended position. In some embodiments, the bearing arm flywheel 130 rotation and resulting bearing movement on the ramp feature or ramp portion may cause the cam or cam assembly 120 to be pushed from the retracted position towards the extended position, as is illustrated by reference number 172 in FIG. 1F. In some embodiments, the bearing arm 130 rotation may drive the bearing 135 along a sloping path on a ramp portion or ramp feature of the cam or cam assembly 120. In some embodiments, the ramp portion may be located on a bottom section or portion of the cam or cam assembly 120. In these embodiments, the driving of the bearing 135 along the sloping path of the ramp portion of the cam assembly drives the cam or cam assembly 120 from the retracted to the extended position. In some embodiments, the cam or cam assembly may be positioned or pressed against (or connected) the needle or needle plunger 110 and push the needle or needle plunger 110 and the needle may move from a retracted position (as shown in FIG. 1C and FIG. 1E) to an extended position (as shown in FIGS. 1D and 1F).

In some embodiments, the ramp feature or ramp assembly may have many different shapes or waveforms, and/or different dimensions which would be associated with different behaviors of the needle including dwell time of the needle. In some embodiments, if a ramp feature or ramp shape is flat and the bearing 135 is moving along the ramp feature, the cam or cam assembly 120 is not moving down the motor shaft cam and thus the needle is still in the retracted position. However, if the ramp feature has any incline or slight curve then the bearing 135 pushes the cam or cam assembly 120 up or down the motor shaft 141 and cause the needle 110 to move towards the extended position. In some embodiments, the rise or slope of the ramp feature or ramp assembly may determine how quickly or fast the cam 120 moves along the motor shaft relative to the rest of the stroke cycle 141 and the needle 110 moves from the retracted portion to the extended position. Similarly, on an opposite side of the ramp feature or a different section of the ramp feature, the bearing 135 may move along the slope or decline of the ramp feature on the opposite side and may cause the cam or cam assembly 120 to move back up the motor shaft 141 and cause the needle 110 to move to the retracted position. In some embodiments, the shape, waveform and/or the slope of one portion of the ramp feature may be symmetrical with the other portion of the ramp feature. In some embodiments, the shape, waveform and/or the slope of one portion of the ramp feature may be different and thus not symmetrical with the other portion and this may be referred to as an asymmetrical cam or cam assembly 120.

In some embodiments, the cam or cam assembly 120 may have one or more slots (or a plurality of slots) located about a circumferential edge of the cam or cam assembly 120. In some embodiments, an anti-rotation pin 165 may be positioned or located in one of the plurality of slots. In this embodiment, the anti-rotation pin 165 may be attached to the inner housing 145 and does not move. In this embodiment, the anti-rotation pin 165 may fit into one of the slots and the cam or cam assembly 120 may be prevented from rotating when the motor shaft is rotating. In some embodiments, the tattoo machine or device 100 may have more than one anti-rotation pins 165 where each of the anti-rotation pins 165 that fit into the one or more openings or slots. The use of one or more slots on the cam or cam assembly 120 allows the anti-rotation pins to fit into a number of slots and thus does not require a specific location within the rotary tattoo machine or for the cam assembly 120 to have a specific position.

In some embodiments, an RCA jack (or power input port) 155 may be connected or attached to an end cap 150. This allows connection of the tattoo machine or device to an external power supply. In some embodiments, one or more wires may be used to connect the electrical jack 155 to the electric motor 140. In some embodiments, a cable may be plugged from an external tattoo power supply to the RCA jack 155 to provide power to the tattoo machine or device. In some embodiments, the rotary tattoo machine or device 100 may be turned on utilizing an external foot switch or another switch. In some embodiments, a battery may be used to provide power to the tattoo machine or device.

In some embodiments, one or more springs 160 may be placed inside a grip or outer housing 125. In some embodiments, a first end of the one or more springs 160 may be in contact with an end of grip or outer housing 125 and a second or other end of the one or more springs 160 in contact the cam or cam assembly 120. In some embodiments the one or more springs 160 may be positioned around the protruding portion of the cam or cam assembly 120, the needle or needle plunger 110 and/or a portion of the needle cartridge 105. In some embodiments, the one or more springs 160 returns the cam or cam assembly 120 to a retracted position (or at rest position) from an extended position or where the needle is in the consumer's skin). In addition, the one or more springs 160 holds and/or presses the cam or cam assembly 120 in place against the bearing 135 of the bearing arm or flywheel 130.

In some embodiments, the cam or cam assembly 120 may be utilized to drive the needle cartridge assembly 105 and needle 110 in an up or down direction. In some embodiments, the needle cartridge may be connected or attached to the outer housing. In some embodiments, the one or more rubber O-rings 115 and 116 may be attached or connected to the inner housing and the one or more O-rings may be utilized to set a distance and/or position between the inner housing 145 and/or the outer housing 125. In some embodiments, a rear O-ring 116 may be placed in a position closer to a back of the tattoo machine as compared to the front friction O-ring 115. In some embodiments, the rotary tattoo machine or device 100 may utilize a needle bar and the needle 110 may be held by the needle bar. In these embodiments, the cam or cam assembly 120 may contact or push the needle bar when it moves up and down the motor shaft 141.

FIGS. 2A-2M illustrate different cam or cam assemblies according to embodiments of the invention. These figures are illustrative and are only representative of some of the cams or cam assemblies that are possible with the subject matter described herein. In some embodiments, a cam or cam assembly 120 may be identified by one measurement which is an amount of time (e.g., a dwell time) of a stroke cycle a needle spends in a consumer's skin or in the extended position. In some embodiments, this dwell time may be represented by a percentage. In some embodiments, different cam or cam assemblies 120 have dwell times or percentages ranging from 10 percent to 55 percent. In some embodiments, for example, one cam or cam assembly 120 may have a 20 percent label which represents that the needle spends approximately 20 percent of a stroke cycle inside a consumer's skin. In a second example, one cam or cam assembly 120 may have a 33 percent label which represents that the needle spends approximately 33 percent of a stroke cycle inside a consumer's skin.

In some embodiments, a cam or cam assembly 120 may be identified by another measurement which is a distance or estimated distance a needle may travel during a stroke cycle (e.g., which may be referred to as a stroke length). In some embodiments, a stroke length may range from 0.5 millimeters to 6.5 millimeters. Accordingly, in some embodiments, each cam or cam assembly 120 may be referred to as 4.2 or alternatively 3.5 or 2.8 millimeters. In some embodiments, a height of a ramp or ramp shape on one end of a cam or cam assembly 120 may correspond to a stroke length of the cam or cam assembly 120. As noted above, these measurements are only illustrative and/or representative examples and may have a lot of other values.

Other rotary tattoo machines do not utilize a cam or cam assembly as described herein. This new and novel assembly is a significant improvement over prior tattoo machine devices because a tattoo artist or operator now may control a dwell time (or percentage) of a needle inside of a consumer's skin or in an extended position and/or a stroke length of the needle by changing to a different cam or cam assembly.

FIG. 2A illustrates a top view of a cam assembly having a stroke length of approximately 4.2 millimeters and a 28% dwell time according to some embodiments. FIG. 2B illustrates a side view of a cam assembly having a stroke length of approximately 4.2 millimeters and a 28 percent dwell time according to some embodiments. FIG. 2C illustrates a front cross-section view of a cam assembly having a stroke length of approximately 4.2 millimeters and a 28 percent dwell time according to some embodiments.

In some embodiments, a cam or cam assembly 120 may include one or more slots 205, a protrusion or shaft receiving assembly 220, a ramp feature or ramp assembly 210, and/or an opening 215 in a center of the cam or cam assembly 220. In some embodiments, the cam or cam assembly 120 may have a circular shape when viewed from the top. In some embodiments, a protrusion or shaft receiving assembly 220 may have opening to allow the motor shaft 141 to be placed and/or positioned. In some embodiments, the cam or cam assembly 120 may have one or more slots 205 around the circumferential edge of the cam or cam assembly 120. These one or more slots 205 may engage the anti-rotation pin to prevent the cam or cam assembly 120 from rotating. In some embodiments, for example as illustrated the ramp feature or ramp assembly 210 may have a height of approximately 4.2 millimeters. In some embodiments, the height of the ramp or ramp assembly 210 may determine or be associated with a stroke length of the rotary tattoo machine. In other words, in some embodiments, a tattoo operator or artist may modify and/or change a stroke length of the rotary tattoo machine by changing the cam or cam assembly 120 to one that has a different ramp feature or ramp assembly height.

In some embodiments, a ramp feature or ramp assembly 210 shape, waveform and/or slope may control a dwell time (or percentage) of the needle in a rotary tattoo machine in a consumers skin or in an extended position. In some embodiments, the ramp feature or ramp assembly 210 and the protrusion 220 may be on opposite ends or sides of the cam or cam assembly 120. In some embodiments, the ramp feature or ramp assembly 210 may have a slope that is a sharp or steep curve from a bottom portion of the ramp assembly (as illustrated in FIG. 2B) to a top portion of the ramp assembly. In this embodiment, the sharp or steep curve allows the bearing 135 to travel from a lowest point of the ramp assembly to a highest point of the ramp assembly 210 in a quick fashion. In this embodiment, the quick travel time allows a quicker movement of the needle 110 to an extended position and also a quicker movement of the needle to a retracted position (if the back side of the ramp feature is symmetrical with the illustrated portion 211 of the ramp feature or ramp assembly. In this embodiment, the quicker movement to the extended position and then back to the retracted position results in a lower or smaller dwell time in the consumer's skin or in an extended position. Thus, the dwell time is associated and/or controlled by shape and/or slope of the ramp feature or ramp assembly 210. FIG. 2C illustrates that a cross section of the cam or cam assembly 120 from a front view. FIG. 2C illustrates the motor assembly shaft 141 that is placed or positioned in the opening 215 of the cam assembly. In addition, in this embodiment, the cam assembly 120 ramp features, ramp portions or ramp assemblies are symmetrical (e.g., they have the same dimension and shapes). In FIG. 2C, a left portion of the ramp feature 211 and a right portion of the ramp feature 212 cam assemblies are symmetrical.

FIG. 2D illustrates a top view of a cam or cam assembly having a stroke length of approximately 4.2 millimeters and a 40% dwell time according to some embodiments. FIG. 2E illustrates a side view of a cam or cam assembly having a stroke length of approximately 4.2 millimeters and a 40% dwell time according to some embodiments. FIG. 2F illustrates a front cross-section view of a cam or cam assembly having a stroke length of approximately 4.2 millimeters and a 40 percent dwell time according to some embodiments.

The main difference between the cam or cam assembly in FIGS. 2A-2C and the cam or cam assembly in FIGS. 2D-2F is the different shape and/or slope of the ramp feature or ramp assembly of the cam or cam assembly 120 in FIGS. 2D-2F. In the embodiments illustrated in FIGS. 2E and 2F, the slope of the ramp feature or ramp assembly is lesser and/or lower. This results in a longer time where the cam assembly is pushing the needle and also causes the needle to dwell a longer time in the consumer's skin or in an extended position. Thus, this embodiment is associated with the dwell time of approximately 40 percent in a consumer's skin or in the extended position. Also, the cam assembly 120 illustrated in FIGS. 2D-2F is symmetrical as is shown in FIG. 2F where ramp assemblies 217 and 212 are the same on each side.

Figure 2G:
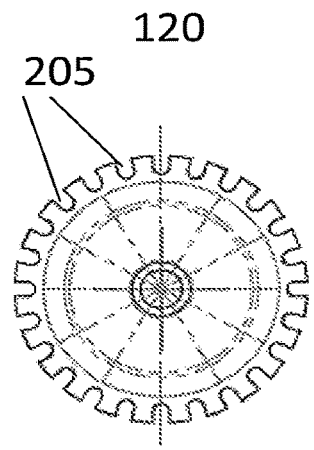
FIG. 2G illustrates a top view of a cam assembly having a stroke length of approximately 4.2 millimeters and a 33% dwell time according to some embodiments.
Figure 2H:
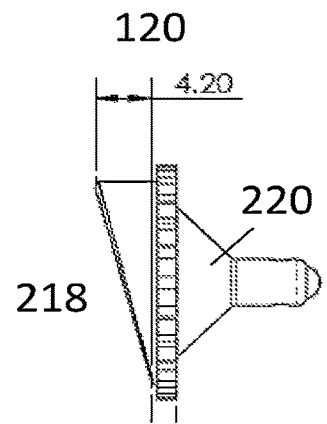
FIG. 2H illustrates a side view of a cam assembly having a stroke length of approximately 4.2 millimeters and a 33% dwell time according to some embodiments.
Figure 2I:
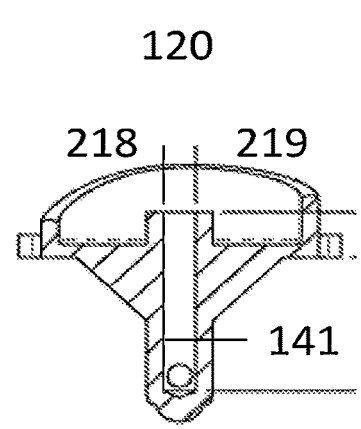
FIG. 2I illustrates a front cross-section view of a cam assembly having a stroke length of approximately 4.2 millimeters and a 33 percent dwell time according to some embodiments.

FIG. 2G illustrates a top view of a cam or cam assembly having a stroke length of approximately 4.2 millimeters and a 33% dwell time according to some embodiments. FIG. 2H illustrates a side view of a cam or cam assembly having a stroke length of approximately 4.2 millimeters and a 33% dwell time according to some embodiments. FIG. 2I illustrates a front cross-section view of a cam or cam assembly having a stroke length of approximately 4.2 millimeters and a 33 percent dwell time according to some embodiments. FIG. 2H illustrates a ramp feature or ramp assembly 218 of a cam or cam assembly 120 that has a greater slope than the ramp slope for the cam or cam assembly illustrated in FIGS. 2A-2C and a lower slope than the ramp slope for the cam or cam assembly 120 illustrated in FIGS. 2D-2F. This results in a bearing 135 for the cam or cam assembly illustrated in FIGS. 2G-2I moving to an extended position in a quicker amount of time as compared to the cam or cam assembly illustrated in FIGS. 2D-2F, but in a slower or slightly slower time than the cam or cam assembly illustrated in FIGS. 2A-2C. In addition, the cam or cam assembly 120 illustrated in FIG. 2I is asymmetrical in that the slope and/or shape of the two sides 218 and 219 of the ramp feature or ramp assembly 221 are different. This means that the two sides 218 and 219 will result in the needle 110 having different associated dwell times in the consumer skin. It also shows that different sides of the ramp feature or ramp assemblies may have different shapes and/or different dimensions and thus different dwell times. This means that moving from the needle from the retracted position to the extended position may have specific dwell time characteristics and the movement from the extended position back to the retracted position may have a different dwell time. This provides great flexibility in designing of rotary tattoo machines and the ability to handle different types of tattoos or different portions of the tattoos because you have cams or cam assemblies that may be designed to be associated or correspond to different types of tattoos or different sections of the tattoos.

Figure 2J:
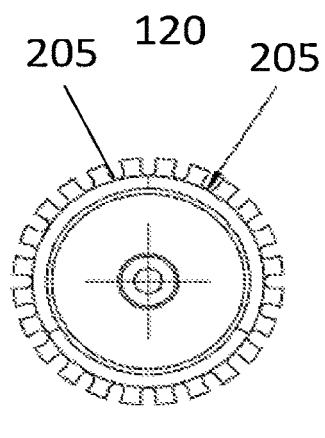
FIG. 2J illustrates a top view of a cam or cam assembly having a stroke length of approximately 4.2 millimeters and a 20% dwell time according to some embodiments.
Figure 2K:
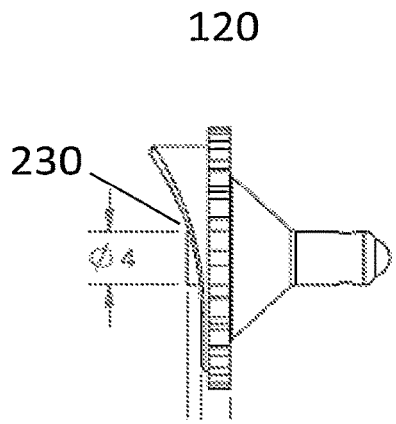
FIG. 2K illustrates a side view of a cam or cam assembly having a stroke length of approximately 4.2 millimeters and a 20% dwell time according to some embodiments.
Figure 2L:
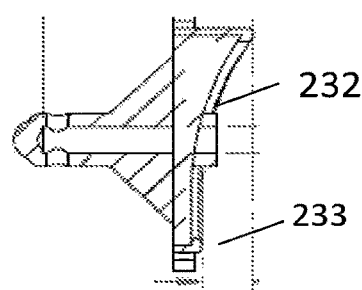
FIG. 2L illustrates a side cross-section view of a cam or cam assembly having a stroke length of approximately 4.2 millimeters and a 20 percent dwell time according to some embodiments.

FIG. 2J illustrates a top view of a cam or cam assembly having a stroke length of approximately 4.2 millimeters and a 20% dwell time according to some embodiments. FIG. 2K illustrates a side view of a cam or cam assembly having a stroke length of approximately 4.2 millimeters and a 20% dwell time according to some embodiments. FIG. 2L illustrates a side cross-section view of a cam or cam assembly having a stroke length of approximately 4.2 millimeters and a 20 percent dwell time according to some embodiments. In FIG. 2J, the cam or cam assembly 120 may include one or more slots 205. In FIG. 2K, the cam or cam assembly 120 may include a ramp feature or ramp assembly 230 that corresponds to the smallest amount of dwell time in a consumer's skin or in an extended position. As is illustrated in FIGS. 2K and 2L, a first portion 233 of the ramp feature 230 may be flat and thus the cam or cam assembly 120 may not move up and down the motor shaft and thus the needle may not be inserted into the consumer's skin or to an extended position. As is illustrated in FIGS. 2J and 2K, a second portion 233 of the ramp feature may have a slope or shape and this may result in the needle moving to the extended position from the retracted position. Because the ramp feature moves to the highest point in a smaller space (e.g., approximately half of a size of the ramp assembly 230), this results in a smallest amount of dwell time or time in an extended position for the tattoo needle. The embodiments illustrated in FIGS. 2K and 2L identify that even one side of a ramp assembly 120 may have different shapes or slopes in order to control dwell times or times in an extended position for the needle.

In some embodiments, cams or cam assemblies 120 with different dwell times or percentages of stoke cycle inside a consumer's skin may be utilized for different tattoo types or sections of a tattoo. For example, a cam assembly or cam 120 having a small dwell time (e.g., approximately 20 percent), may have a quick or snappy needle insertion along with a fast recoil which results in a needle getting in and out of a consumer's skin very quickly. In these embodiments, the cam assemblies or cam 120 having shorter or small dwell times may be utilized by a tattoo artist who is providing a tattoo lining or may be utilized by a tattoo artist or operator who moves their hand very quickly across a tattoo or work area on a consumer's skin. In these embodiments, the slope and/or shape may be lower and allow a bearing to more easily move up the ramp assembly 210.

In another example, a cam or cam assembly 120 having a medium dwell time (e.g., approximately 28 percent) may also have a slightly slower needle insertion speed with a similar fast recoil as the 20 percent embodiment. In this embodiment (e.g., a 28 percent to 33 percent cam), these cam assemblies 120 (and thus the tattoo machine or devices)

may be utilized for tattoo shading or may be utilized by tattoo artist or operator whose hand does not move as quickly across the consumers skin).

In some embodiments, a cam assembly or cam 120 having a medium dwell time (e.g., approximately 33 percent) may have a much slower insertion speed with a same recoil speed as the cam assembly or cam 120 with a dwell time of 20 percent. In some embodiments, this cam assembly 120 may be asymmetrical. In this embodiment (e.g., the approximately 33% cam assembly) may be used for tattoo layering and/or other tattooing over a same area of a consumer's skin multiple times without damaging the consumer's skin tissue.

In some embodiments, a cam assembly or cam 120 having a large dwell time (e.g., approximately 40 percent) may have a slowest skin insertion speed. In this embodiment (e.g., the approximately 40% cam assembly) may be used for coloring and/or other tattooing where solid areas of saturation are needed.

Figure 2M:
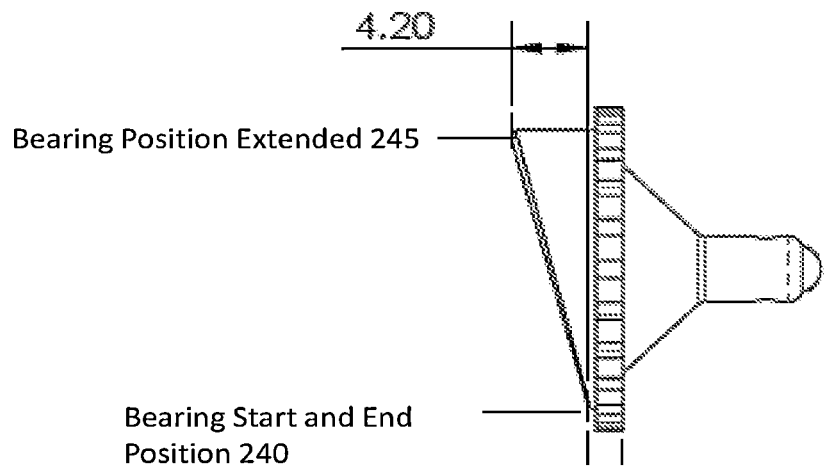
FIG. 2M illustrates a side view of a cam or cam assembly according to some embodiments.
Figure 2N:
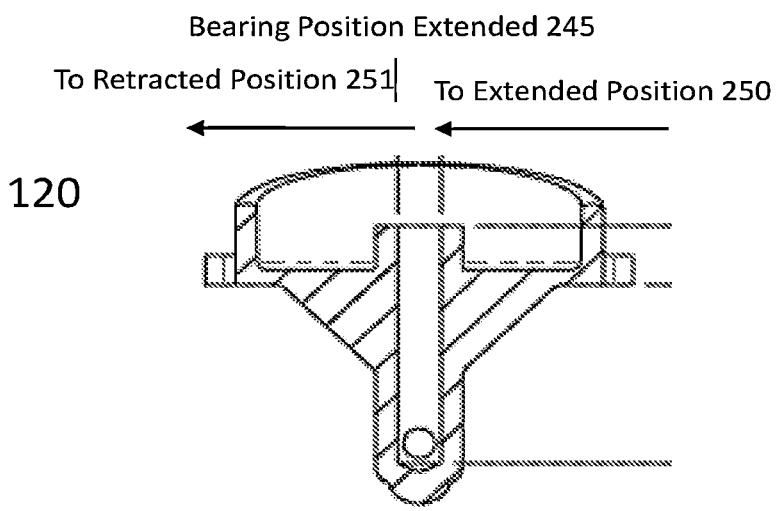
FIG. 2N illustrates a cross sectional view of a cam or cam assembly according to some embodiments

The bearing travels along the ramp feature or ramp assembly of the cam assembly as follows. This is illustrated in FIGS. 2M and 2N which are a side view and a cross sectional view according to some embodiments. FIG. 2M illustrates a side view of a cam or cam assembly according to some embodiments. FIG. 2N illustrates a cross sectional view of a cam or cam assembly according to some embodiments. In some embodiments, the bearing moves from a start position 240 (where the needle is retracted) to an extended position 245 (where the needle is extended). After that, the bearing moves from the extended position 245 back to the start position utilizing another portion of the ramp feature or ramp assembly of the cam or cam assembly. This is illustrated in FIG. 2M where the bearing movement to the extended position along the ramp feature or ramp assembly is illustrated by arrow and reference number 250 and the bearing movement from the extended position to the end position (which may be the start position) along the ramp feature or ramp assembly is illustrated by arrow 251. Because FIG. 2K is a cross-section, you cannot see that actually the bearing travels on a circular path from a retracted position to an extended position and then to a retracted position around the circular path (e.g., in other words the bearing moves in one direction—e.g., clockwise or counterclockwise).

In some embodiments, the rotating tattoo machine or device may also include a mechanism or switch that reverses a rotation of the motor or motor assembly 140 and thus reverses a rotation direction of the shaft or shaft assembly 141. Thus, in this embodiment, the cam or cam assembly 120 may be dual-purpose if the motor assembly 140 may rotate in both directions. In this embodiment, when the motor 140 is rotating in one direction, one portion of a ramp feature or ramp assembly of the cam or cam assembly may be utilized (e.g., in FIG. 2I, ramp feature portion or ramp assembly portion 218 of the cam or cam assembly may be utilized) which results in a first dwell time (which may be utilized for tattoo lining). In this embodiment, the second portion of the ramp feature or ramp assembly may be utilized for the return of the needle to the retracted position (e.g., in FIG. 2I, ramp assembly portion 219 of the cam assembly may be utilized), which results in a second dwell time (which may be utilized for tattoo saturating). This occurs because the cam or cam assembly illustrated in FIGS. 2G-2I is asymmetrical (e.g., has a different waveform, shape, slope, and/or dimensions for different sections or portions of the ramp assembly). As is illustrated in FIG. 2I, a ramp feature or ramp assembly portion 218 has a different waveform, shape and/or slope as compared to ramp portion 219. Because the different ramp portions have different waveforms, shapes and/or slopes, the pushing and/or extending of the needle could be faster on one ramp feature or ramp assembly portion of the cam assembly (e.g., ramp portion 218 which has a lower slope and thus easier path), and the pushing and/or extending of the needle could be slower when the other ramp feature or ramp assembly portion is being utilized (e.g., ramp feature or ramp assembly portion 219 which has a higher slope and a more difficult path). The cam in some cases has an asymmetrical waveform, so for example the side that does the pushing (extending) of the needle could be fast, while the side doing the retracting of the needle can be slow. However, if the rotation of the motor assembly 140 is reversed, then a different path is taken on the ramp feature or ramp assembly by the bearing. In these embodiments, reversing the rotation of the motor assembly to a counterclockwise direction (from a clockwise direction), would cause the pushing or extending of the needle to be performed by the one side of the ramp feature or ramp assembly (e.g., ramp feature portion 219 in FIG. 2I) and retracting performed by the back side of that ramp feature (e.g., ramp feature portion 218 in FIG. 2I). The reversing of the motor assembly may do two things: For asymmetrical cam assemblies, the cam or cam assemblies can be dual-purpose. For symmetrical cams, this can double or extend the lifespan of these cam assemblies because when one side of the ramp assembly is worn out, the other side of the ramp assembly may be used.

When the rotary tattoo machine or device is fully assembled, a needle cartridge 105 may be attached to the end of the outer housing of the rotary machine or device 100 and the needle may be located in the needle cartridge 105. In some embodiments, a knob on an end cap 150 may be utilized to adjust a depth of the needle 110. In some embodiments, the needle 110 may be dipped into an inkwell or ink container and may then be utilized to apply the ink to the user or consumer's skin.

It is important to sterilize or decontaminate the rotary tattoo machine or device 100 between uses, especially with an environment including infectious diseases. In some embodiments, an autoclave machine or device may be utilized to sterilize some or all of the portions of the rotary tattoo machine or device 100. In some embodiments, a consumer may remove the grip and/or the outer housing by unscrewing or unfastening the grip and/or the outer housing from the inner housing 145. In some embodiments, the grip 125 and/or the outer housing may be placed into a sterilization pouch and the sterilization pouch may be run through the autoclave machine. It is important to sterilize the grip or outer housing 125 because this is the part of the rotary tattoo machine or device 100 that the tattoo artist touches. In some embodiments, the grip 125 and/or the outer housing may be disposable and then disposed of after each use.

A unique aspect of the present rotary tattoo machine or device is the ability to vary the needle frequency waveform and/or to minimize a portion of the stroke cycle that the needle may be present within a consumer's skin or an extended portion. Frequency waveform may refer to the position of the needle or cam in a given cycle over time. In some embodiments, a portion of the stroke cycle may be represented and/or measured as a percentage. The varying of the needle frequency waveform may be accomplished by the rotary tattoo machine having a replaceable cam or cam assembly 120 with different dimensional characteristics and/or or ramp slope and/or shape characteristics. In some embodiments, a tattoo artist may remove the grip 125 and/or outer housing and then remove the cam or cam assembly 120. In these embodiments, the original cam or cam assembly 120 may be replaced with another cam or cam assembly 120 having a different waveform and/or stroke profile or a different ramp slope and/or shape. In some embodiments, as described above, the different waveform and/or stroke profile may be accomplished via different dimensional characteristics or aspects (including but not limited to the shape or slope of the ramp or ramp assembly of the cam or cam assembly). In these embodiments, the tattoo artist may then attach or connect the grip 125 and/or outer housing to the inner housing 145. After the cam or cam assembly 120 has been replaced, the rotary tattoo machine or device 100 now has a different needle frequency waveform and/or stroke profile because of the different cam or cam assembly 120.

A tattoo artist may also change the stroke length of the rotary tattoo machine or device 100. In order to change the stroke length, the tattoo artist may first remove the grip and/or outer housing 125 from the inner housing 145 by unscrewing the two, using the outer housing and end cap grip 150. In this embodiment, the tattoo artist may remove the cam or cam assembly and replace it with the desired cam or cam assembly 120 with a desired or selected stroke length. For example, cam assemblies may have stroke lengths of 2.8, 3.5 or 4.2 millimeters, or alternatively have stroke lengths ranging from 0.5 millimeters to 6.5 millimeters, although the claimed subject matter is not limited to these stroke lengths. In some embodiments, the tattoo artist may screw the grip/outer housing 125 back onto the inner housing 145, which is accomplished by using the grip/outer housing 125 and end cap 150 to grip and unscrew. In some embodiments, the stroke length associated with a cam assembly 120 may be identified by a real numeral which may be expressed in millimeters.

A tattoo artist may also adjust a speed of the rotary tattoo machine or device by changing the voltage of the rotary tattoo machine or device, while it is plugged in and operating, through a variety of well known techniques. In some embodiments, a tattoo artist may also replace and/or change a motor assembly 140 in order to change the speed, torque, and/or power characteristics of the rotary tattoo machine or device. In some embodiments, a different motor assembly 140 may provide a higher rotational speed than a prior motor assembly and/or may generate a higher torque as compared to the prior motor assembly.

The new and improved rotary tattoo machine or device may be made utilizing a number of molded parts. In some embodiments, the Grip/Outer Housing 125, the Inner Housing 145, the Bearing Arm or Flywheel 130, the Cam or Cam Assembly 120, and/or the End Cap 150 may be machine molded. In some embodiments, these components may be made of a plastic material or a composite material. In some embodiments, the above-identified components may be made of a metallic material, for example aluminum, steel, and/or brass. In some embodiments, motor or motor assembly 140 may be a 2224 custom-made electric motor sold by Faulhaber, although the claimed subject matter is not limited to this motor and other electric motors. In this embodiment, the motor or motor assembly 140 may include ball bearings and/or a 12-14.6 mm exposed shaft or longer, or shaft assembly 141 (although other motors or motor assemblies with other shaft lengths may be utilized). For example, the shaft length may range from 10 mm to 20 mm in some embodiments. In some embodiments, the cam function(s) may be utilized using a pneumatic or hydraulic motor. In some embodiments, the bearing 135, the spring 160, the set screw, the one or more machine screws, the electrical jack (RCA) or connector 155, and/or the anti-rotation pin 165 may be obtained from other manufacturers and/or distributors.

Figure 3:
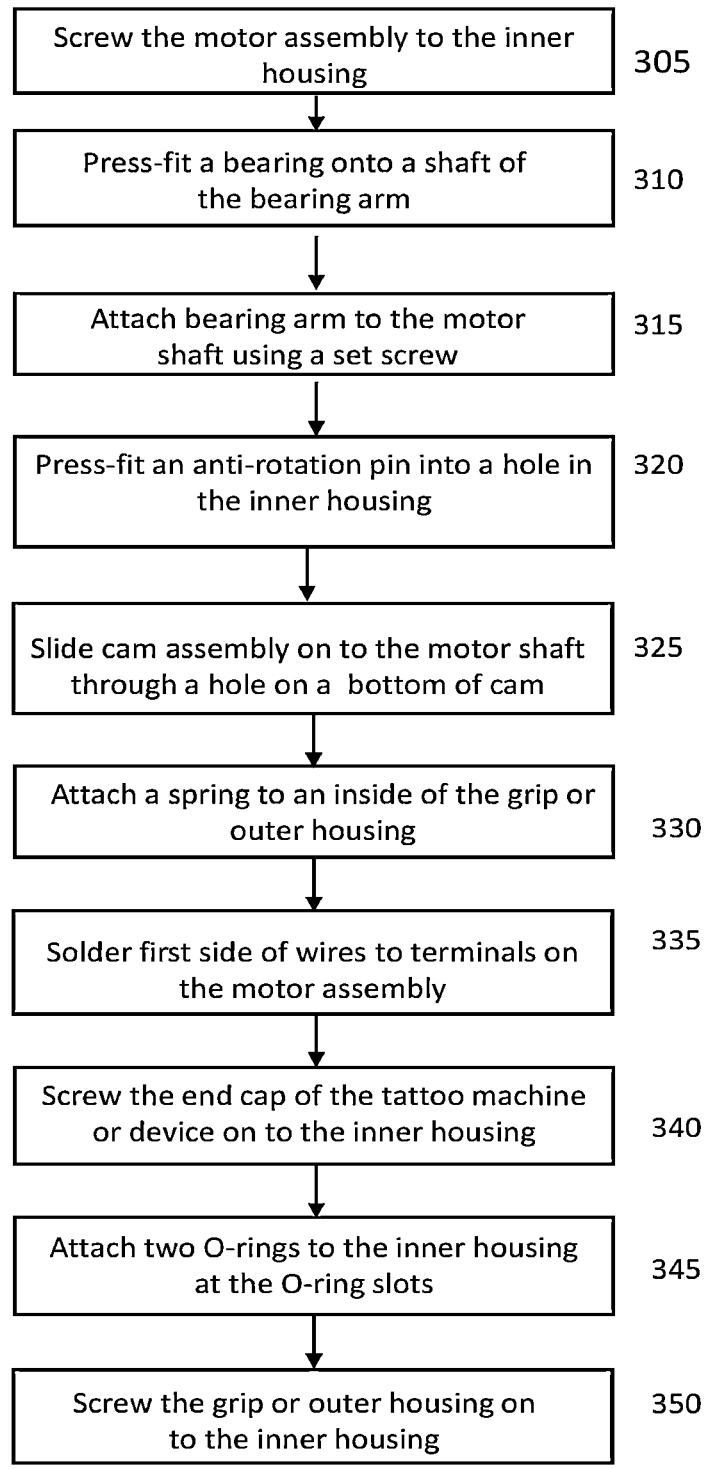
FIG. 3 illustrates a flowchart illustrating assembly of a rotary tattoo machine or device according to some embodiments.

FIG. 3 illustrates a flowchart illustrating assembly of a rotary tattoo machine or device according to some embodiments. A tattoo artist may assemble the rotary tattoo machine or device 100 by following the following steps. In step 305, a tattoo artist or individual may screw the motor or motor assembly 140 to the inner housing 145 utilizing three (3) machine screws. Depending on the embodiment, more or less machine screws may be utilized and/or other fasteners may also be utilized.

In step 310, a tattoo artist or manufacturer may press-fit a bearing 135 onto a shaft of the bearing arm 130. In step 315, the tattoo artist or manufacturer may attach the bearing arm 130 to the motor shaft 141 using a set screw, at a bottom of the motor assembly shaft 141. In step 320, the tattoo artist or manufacturer may press-fit an anti-rotation pin 165 into a hole in the inner housing 145 until the anti-rotation pin 165 reaches a bottom of the hole. In step 325, the tattoo artist or manufacturer may slide a cam or cam assembly on to the motor shaft or motor shaft assembly 141 through a matching size hole on a bottom of the cam or cam assembly. In some embodiments, it may be important to make sure that the anti-rotation pin 165 slides into one of corresponding slots on the cam 120. In step 330, the tattoo artist or manufacturer may attach a spring 160 to an inside of the grip or outer housing 125 by pushing it into an inner cavity until the spring stops in the channel designed to hold the spring 160. In step 335, the tattoo artist or manufacturer may solder a first side of one or more wires to corresponding terminals on the motor assembly 140 and other sides of the wires to the terminals on a RCA electrical jack 155. In some embodiments, the wires may need to be passing through a hole or channel of the end cap 150 of the tattoo machine or device 100. In step 340, the tattoo artist or manufacturer may screw the end cap 150 of the tattoo machine or device 100 on to the inner housing 145 at an end nearest to the electric motor assembly 140 terminals). In step 345, the tattoo artist or manufacturer may attach two O-rings 115 and 116 to the inner housing 145 into the O-ring slots. In step 350, the tattoo artist or manufacturer may screw the grip or outer housing 125 on to the inner housing 145.

The new and improved rotary tattoo machine has multiple cam or cam assemblies 120 that all fit the tattoo machine and can be swapped out and/or changed. In some embodiments, the multiple cams or cam assemblies 120 have different dimensional and/or shape profiles which change the behavior of the needle(s) with respect to the consumer's skin and/or stroke lengths of the rotary tattoo machine.

Figure 4A:
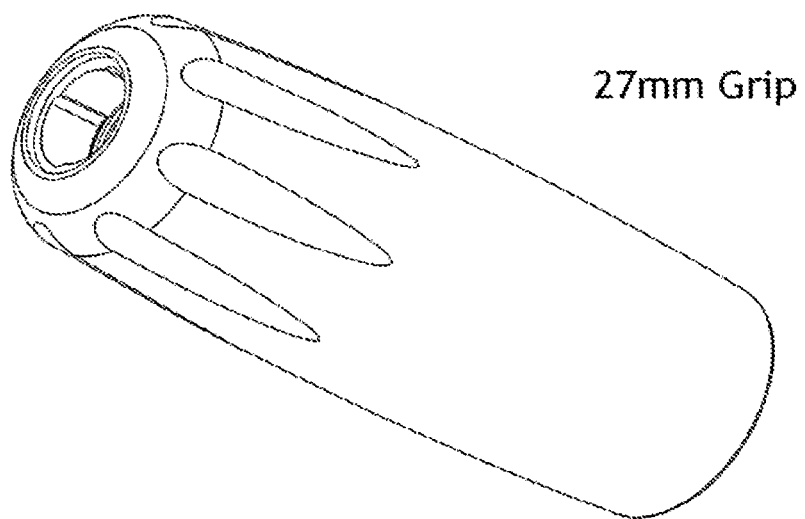
FIG. 4A illustrates a small grip or housing according to some embodiments.
Figure 4B:
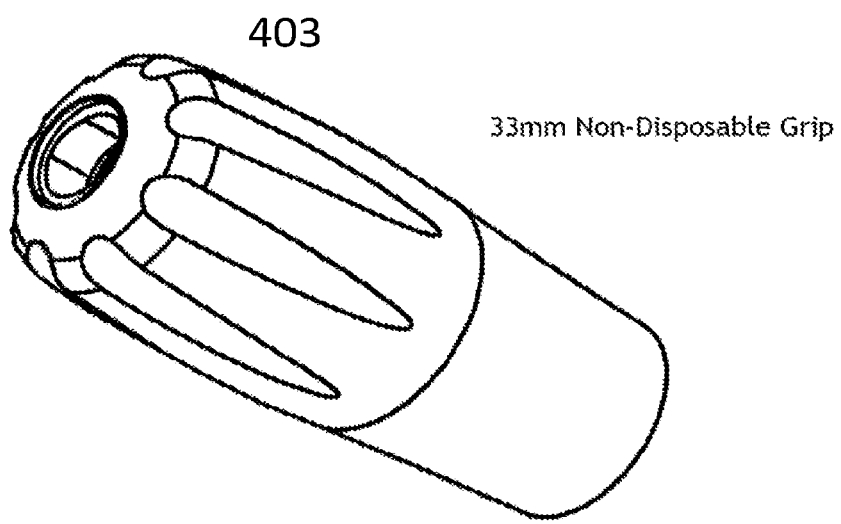
FIG. 4B illustrates a medium grip or housing according to some embodiments.
Figure 4C:
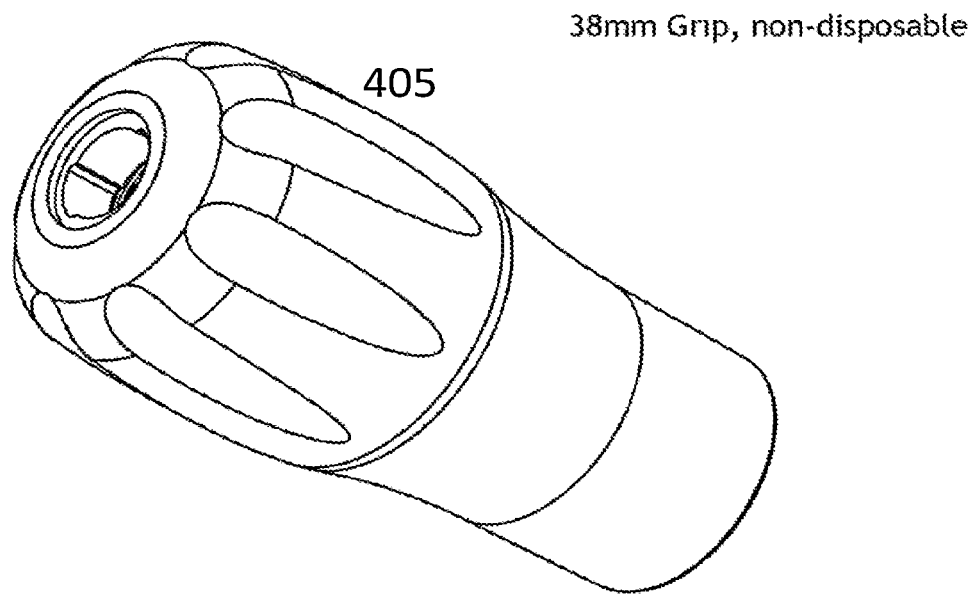
FIG. 4C illustrates a large grip or housing according to some embodiments.
Figure 4D:
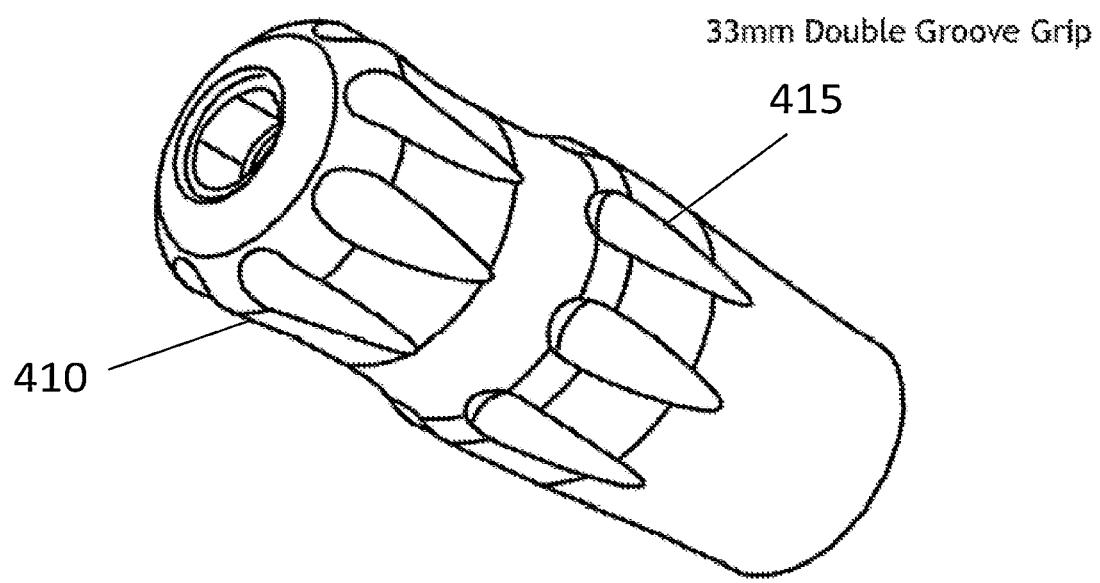
FIG. 4D illustrates a grip or housing with multiple holding positions (e.g., two holding positions) according to some embodiments.
Figure 4E:
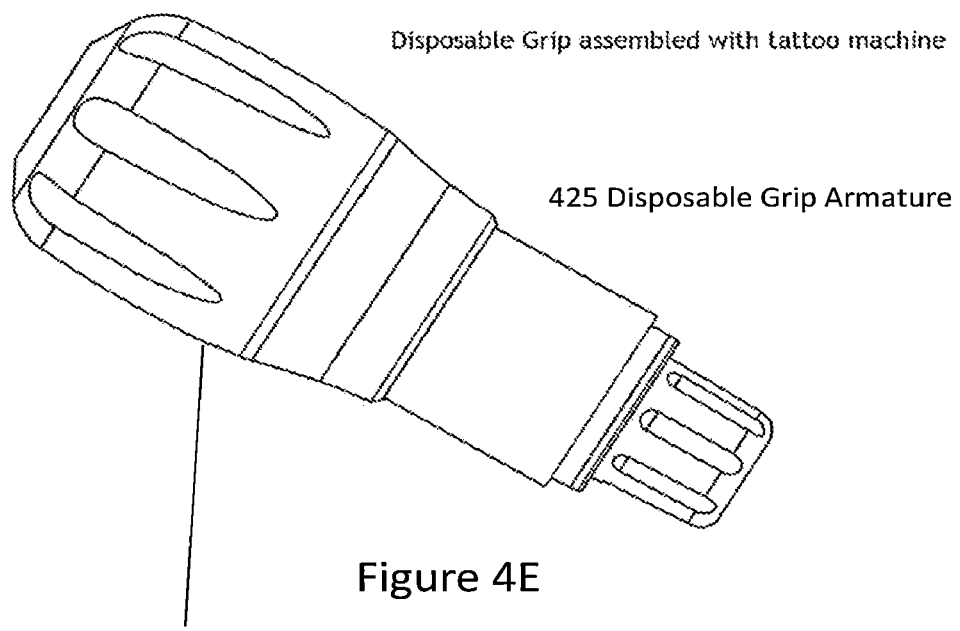
FIG. 4E illustrates a disposable grip or housing assembled in a rotary tattoo machine according to some embodiments.
Figure 4F:
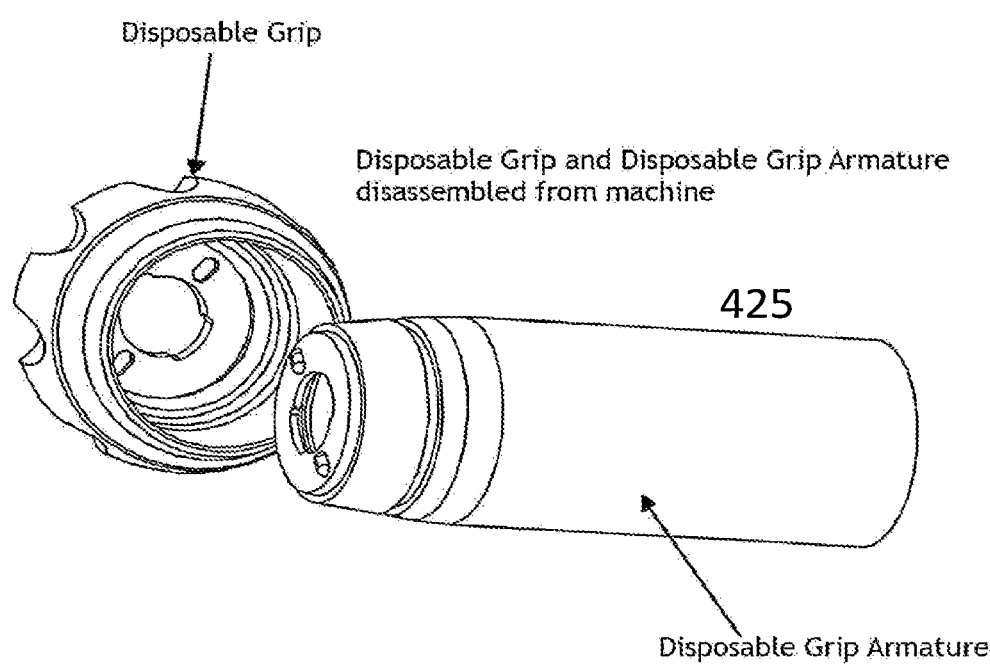
FIG. 4F illustrates a disposable grip or housing in a rotary tattoo machine with the grip removed according to some embodiments.

An additional feature of the new and improved rotary tattoo machine or device 100 may be the ability to utilize multiple grips or outer housings 125 that can be changed and/or swapped out with each other. In some embodiments, the different grips or outer housings 125 may have different sizes and/or shapes. FIG. 4A-4F illustrates different grips or outer housings for a new and improved rotary tattoo machines according to some embodiments. This allows grips or outer housings to be changed if a tattoo artist has a larger hand or may need a better grip in order to apply ink to the user or consumer. In some embodiments, the grips or outer housings may have different sizes and/or different shapes. In an embodiment, a grip shape may have an ergonomic purpose. In an embodiment, the grip may allow better comfort for the tattoo artist. In an embodiment, the grip or outer housing may have multiple holding positions. In an embodiment, the grip or outer housing 125 may be disposable and there may also be a disposable grip cover, which may be utilized to address sanitary concerns of consumers. In this embodiment, if the tattoo artist utilizes the disposable grip and the disposable grip cover, there is no need to clean the grip 125 between each tattoo and this is advantageous when dealing with consumers who want a clean tattoo practice. In embodiments, where grips or outer housings 125 are disposable, the grip or outer housings 125 of the rotary tattoo machines may always be clean. This may eliminate the need to autoclave the grip or outer housings. In an embodiment, the grip or outer housing 125 may be an anti-roll grip, or a larger or smaller size grip to accommodate a bigger or smaller motor assembly 140. FIG. 4A illustrates a small grip or housing according to some embodiments, which may be a 27 mm grip or housing 401. FIG. 4B illustrates a medium grip or housing according to some embodiments. In some embodiments, the medium grip or housing for the rotary tattoo machine may be a 33 mm grip or housing 403. FIG. 4C illustrates a large grip or housing according to some embodiments. In some embodiments, the large grip or housing for the rotary tattoo machine may be a 38 mm grip or housing 405. FIG. 4D illustrates a grip or housing with multiple holding positions (e.g., two holding positions) according to some embodiments. In some embodiments, the grip or housing has a first holding position 410 and a second holding position 415. FIG. 4E illustrates a disposable grip or housing assembled in a rotary tattoo machine according to some embodiments. FIG. 4F illustrates a disposable grip or housing in a rotary tattoo machine with the grip removed according to some embodiments. FIGS. 4E and 4F illustrate a disposable grip or housing 420 and a disposable grip armature 425.

In some embodiments, a tattoo artist may choose to use a traditional needle bar instead of a needle cartridge. In this embodiment, the cam assembly may attach to the needle bar which in turn causes movement of the needle.

In some embodiments, the tattoo machine or device may have a motor or motor assembly 140 that is soft-mounted or mounted onto a spring mechanism that is in the inner housing 145. In some embodiments, the soft-mounting or the mounting onto a spring mechanism of the motor assembly has the purpose of having a cushioning effect for the motor 140. In additional embodiments, the motor or motor assembly 140 can be mounted on a rubber cushion rather than being hard-mounted within the inner housing 145, for the purpose of having a cushioning effect, as described above. In additional embodiments, the motor or motor assembly 140 can be mounted on an adjustable spring or rubber cushion within the inner housing. In such an embodiments, the tattoo machine or device 100 may include an adjustment assembly for the adjustable spring or rubber cushion such that an artist can adjust an amount of cushioning effect he or she desires for the motor or motor assembly.

The new and improved rotary tattoo machine and device with the unique cam or cam assembly design as well as other features described above reduces trauma to a consumer's skin because of the reduction of the amount of time a needle or needles may dwell inside the consumer's skin during a stroke cycle. In other words, the device does the work, and an artist should use it as normal, or how they would use any other needle cartridge tattoo machine.

As stated above, rotary tattoo machines cause a needle to dwell/hesitate inside the skin due to the geometry of the cams that are used to drive a needle. This dwell/hesitation time can cause added and unnecessary tissue damage being that an artist's hand is moving forward and a needle is not given sufficient time to be retracted from the skin before such hand movement is made. The invention claimed here solves this problem.

This variable waveform cam invention causes the needle(s) to be retracted from the skin much quicker, reducing trauma inflicted on the skin tissue. This cam can also be changed such that an artist can determine the most effective amount of dwell/hesitation time that occurs in whatever position of the stroke cycle they want, for whatever effect they are aiming to achieve.

The claimed invention differs from what currently exists. There are no similar mechanisms within the tattoo industry to date. Previous mechanism have no way of controlling the amount of dwell/hesitation time or the speed/acceleration of the needle(s) in any position of a stroke cycle. This invention enables an artist to vary the amount of time a needle(s) spends in the skin in order to reduce trauma to skin and in order to best saturate a tattoo.

Many people are unaware that their tattoo machines are causing the needle(s) they are using to dwell/hesitate inside the skin as they are tattooing, and so no measures are in place or being used to reduce the trauma associated with this dwell.

This invention is designed such that the speed/acceleration within a given stroke cycle of the needle(s) used to do a tattoo can be controlled to such a degree that the dwell/hesitation time of said needles inside the skin can be reduced from 40% of a cycle to 20% of a cycle, for example. Additionally, this can be varied such that the best dwell can be determined and achieved for any type or style of tattooing, such as lining, shading, coloring, blackwork, color, and so forth. The claimed subject matter discussed here Includes: 1. Inner Housing. 2. Electric motor. 3. Cam. 4. Bearing arm/flywheel. 5. Grip/Outer Housing. 6. End Cap. 7. Electrical Jack. 8. Spring. 9. Bearing. 10. Set Screw. 11. Machine Screws. 12. Anti-Rotation Pin. 13. Wiring. 14. Rubber O-rings (2).

Item/Step number 2, the electrical motor, is attached to Item/Step number 1, the inner housing, using Item/Step number 11, machine screws. Item/Step number 4, bearing arm/flywheel is attached to the shaft of Item/Step number 2, the electric motor, using Item/Step number 10, a set screw. Item/Step number 4 has Item/Step number 9, a bearing, press fit onto a shaft built into it. Item/Step number 2, the electric motor, has an extended shaft upon which Item/Step number 3, the cam slides up and down. Item/Step number 9, the bearing, being spun around in a circle beneath Item/Step number 3, the cam, drives Item/Step number 9, a bearing, along a sloping path machined or molded into the bottom of Item/Step number 3, the cam, thereby driving it up and down the extended shaft of Item/Step number 2, the electric motor. Item/Step number 12, an anti-rotation pin, being fixedly attached to Item/Step number 1, the inner housing, fits into a slot created in the side of Item/Step number 3, the cam, which prevents it from rotating. Item/Step number 7, an electrical jack, is attached to the end of Item/Step number 6, the end cap, for electrical connection to a power supply. Item/Step number 8, a spring, fits inside Item/Step number 5, the grip/outer housing, with one side of the spring in contact with the end of Item/Step number5, the grip/outer housing, and the other side of the spring in contact with Item/Step number3, the cam, for the purpose of returning the cam to the retracted position as well as holding the cam in place against the bearing of Item/Step number 4, the bearing arm/flywheel. Item/Step number 13, the wiring, is used to connect Item/Step number 7, the electrical jack to Item/Step number 2, the electric motor. Item/Step number 3, the cam, is used to drive a needle cartridge mechanism (already available equipment), which is attached to Item/Step number 5, the grip/outer housing. Item/Step Number 14, the rubber O-rings, are attached to the inner housing before assembly, for the purpose of maintaining the position of which the device operator has set the outer and inner housings.

Using a fully assembled example of this device, attach any needle cartridge to the end of the outer housing. Use the end cap knob to adjust the depth of the needle. Plug in a cable from a tattoo power supply to this device, and turn it on using a foot switch or switch of any type. Proceed to use this tattoo machine for tattooing. If you wish to autoclave the grip/outer housing, remove it completely by unscrewing it from the inner housing. Place it into a sterilization pouch and run it through a pouches autoclave procedure as you would any other pouched instruments.

To vary the needle(s) frequency waveform, remove the grip/outer housing, then remove the cam and replace it with another cam with a different waveform/stroke profile. Then attach the grip/outer housing to the inner housing. The machine now has a different needle frequency waveform/ stroke profile. To change the stroke length, first remove the grip/outer housing from the inner housing by unscrewing the two, using the outer housing and end cap grip, then remove the cam inside and replace it with the desired cam with its associated stroke length, and screw the grip/outer housing back onto the inner housing, again using the grip/outer housing and end cap to grip.

To adjust the speed of the tattoo machine, while it is plugged in and operating, change the voltage of the tattoo machine power supply you are using to power the tattoo machine, just like any other tattoo machine. Machine or mold the Grip/Outer Housing, Inner Housing, Bearing Arm/ Flywheel, Cam, and End Cap. Purchase the 2224 custom-made electric motor from faulhaber, with ball bearings and 14.6 mm exposed shaft. Purchase bearing, spring, set screw, machine screws, electrical jack (RCA), and anti-rotation pin from manufacturers and/or distributors.

Assemble the device by following these directions: Screw the motor to the inner housing using 3 machine screws. Press-fit a bearing onto the bearing arm shaft. Attach the bearing arm to the motor shaft using a set screw, at the bottom of the shaft. Press-fit an anti-rotation pin into the hole in the inner housing until it reaches the bottom of the hole. Slide a cam on to the motor shaft through the matching size hole on the bottom of the cam (be sure that the anti-rotation pin slides into one of the corresponding slots on the cam). Attach a spring to the inside of the grip/outer housing by pushing it into the inner cavity until it stops in the channel designed to hold it. Solder the wiring to the corresponding terminals on the motor and the other sides of the wires to the terminals on the RCA electrical jack (be sure that the wires are going through the hole of the end cap of the tattoo machine). Screw the end cap of the tattoo machine on to the inner housing (the end nearest to the electric motor terminals). Attach two O-rings to the inner housing into the O-ring slots. Screw the grip/outer housing on to the inner housing.

All elements are necessary to complete this device and its assembly and use. Additional cams can be swapped out with included cams which will change the behavior of the needle(s) and/or stroke lengths. Additional grips/outer housings can be swapped out with included Grip/outer housing which will change the size and/or shape of the grip of the device. Disposable Grips/outer housings can be swapped out with the included grip/outer housing for a disposable option, which creates a convenient way of keeping the grip clean.

Additional cams can be swapped out with included cams which will change the behavior of the needle(s) and/or stroke lengths. Additional grips/outer housings can be swapped out with included Grip/outer housing which will change the size and/or shape of the grip of the device. Disposable Grips/outer housings can be swapped out with the included grip/outer housing for a disposable option, which creates a convenient way of keeping the grip clean.

Motor can be soft-mounted, or mounted on a spring mechanism on to the inner housing, for the purpose of having a cushioning effect. Motor can be mounted on a rubber cushion rather than hard-mounted, for the purpose of having a cushioning effect. Motor can be mounted on an adjustable spring or rubber cushion, such that an artist can adjust the amount of cushion effect he or she desires.

To utilize the mechanism this device is capable of, the reduced trauma to the skin, one must simply use this device the same as any other tattooing device, and the included, assembled mechanism will always be reducing the amount of time a needle or needles will dwell inside the skin in a stroke cycle. In other words, the device does the work, and an artist should use it as normal, or how they would use any other needle cartridge tattoo machine.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client or server computing devices. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter. While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all implementations falling within the scope of the appended claims, and equivalents thereof.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including," "incorporating," "includes," "incorporates," and "having" (and their derivatives), as used in the specification and claims, are interchangeable with and shall have the same meaning as the word "comprising.

The invention claimed is:

1. A rotary tattoo machine or device, comprising:
   a tattoo needle;
   an electric motor including a shaft assembly, the shaft assembly configured to rotate when the electric motor is activated;
   a bearing arm including a bearing, the bearing arm fit onto the shaft assembly; and
   a cam, the cam including a plurality of slots around a circumferential edge of the cam, a ramp assembly and a protrusion on an opposite side of the cam with respect to the ramp assembly, the cam configured to move up and down the shaft assembly due to the rotation of the shaft assembly and the bearing arm and a driving of the bearing, the moving of the cam configured to drive the tattoo needle from a retracted position to an extended position.

2. The rotary tattoo machine of claim 1, wherein the cam is configured to be replaced by an alternate cam, the alternate cam having different dimensions or a different shape from the dimensions of or a shape of the cam and the alternate cam configured to have a different amount of dwell time associated with the tattoo needle.

3. The rotary tattoo machine of claim 1, further comprising an anti-rotation pin, the anti-rotation pin configured to stop the cam from rotating when the shaft assembly rotates.

4. The rotary tattoo machine of claim 1, further comprising a spring assembly, one end of the spring assembly attached to an outer housing and another end of the spring assembly connected to the cam, wherein the spring assembly is configured to return the tattoo needle to the retracted position from the extended position.

5. The rotary tattoo machine of claim 4, wherein the spring assembly further is configured to hold the cam in place against the bearing of the bearing arm.

6. The rotary tattoo machine of claim 1, further including two or more O-rings, the two or more O-rings attached to an inner housing and configured to maintain a position of the inner housing with respect to an outer housing.

7. The rotary tattoo machine of claim 1, wherein the electric motor is configured to be changed to an alternate electric motor, the alternate electric motor configured to have a different rotational speed and/or a different torque, to provide different operational aspects to the rotary tattoo machine.

8. A rotary tattoo machine or device, comprising:
   a tattoo needle;
   an electric motor including a shaft assembly, the shaft assembly configured to rotate when the electric motor is activated;
   a bearing arm, the bearing arm fit onto the shaft assembly and the bearing arm configured to rotate with the shaft assembly;
   a bearing fit onto the bearing arm; and
   a cam, the cam including a plurality of slots around a circumferential edge of the cam, a ramp feature, and a protrusion on an opposite side of the cam with respect to the ramp feature, the bearing configured to move up and down the ramp feature due to the rotation of the bearing arm, the movement of the bearing configured to cause movement of the cam along the shaft assembly and the movement of the cam configured to drive the tattoo needle from a retracted position to an extended position.

9. The rotary tattoo machine of claim 8, wherein the cam has a circular shape.

10. The rotary tattoo machine of claim 8, further including one or more anti-rotation pins, the one or more anti-rotation pins configured to prevent the cam from rotating when the shaft assembly rotates.

11. The rotary tattoo machine of claim 8, the bearing arm including an outer surface and an opening, the opening configured to receive the shaft assembly and configured to rotate along with the shaft assembly.

12. The rotary tattoo machine of claim 11, the bearing arm including a post on the outer surface of the bearing arm, wherein the bearing is configured to fit onto the post.

13. The rotary tattoo machine of claim 8, wherein the cam is configured to include the ramp feature on one side, the bearing moving along the ramp feature to cause movement of the cam along the shaft assembly.

14. The rotary tattoo machine of claim 13, the cam further including the protrusion and an opening, the shaft assembly being positioned into the opening and within the protrusion, the protrusion of the cam touching a tattoo needle cartridge plunger or a needle drive bar and configured to cause movement of the tattoo needle.

15. A rotary tattoo machine or device, comprising:
    a tattoo needle;
    an electric motor including a shaft assembly, the shaft assembly configured to rotate when the electric motor is activated;
    a bearing arm configured to include a bearing, the bearing arm fit onto the shaft assembly and configured to rotate with the shaft assembly; and
    an original cam, the original cam including a ramp feature on a first side, a protrusion on a second side, the second side being opposite the first side, and a plurality of slots on a circumferential edge of the original cam, the bearing configured to move along the ramp feature and to cause the original cam to move along the shaft assembly, the moving of the original cam configured to drive the tattoo needle from a retracted position to an extended position,
    wherein a slope or shape or waveform of the ramp feature is configured to control an amount of dwell time for the tattoo needle.

16. The rotary tattoo machine of claim 15, wherein the original cam is configured to be replaced by an alternate cam, the alternate cam having a different ramp feature slope, shape or waveform, which results in a different dwell time for the tattoo needle.

17. The rotary tattoo machine of claim 16, wherein the alternate cam is configured to include a different ramp feature height, wherein the different ramp feature height is configured to cause the rotary tattoo machine to have a different stroke length than a stroke length of the rotary tattoo machine with the original cam.

* * * * *